United States Patent
Klauber et al.

(10) Patent No.: US 10,961,226 B2
(45) Date of Patent: Mar. 30, 2021

(54) PROCESS FOR PURIFICATION OF PYRAZOLPYRIDAZINES

(71) Applicant: BASF SE, Ludwigshafen am Rhein (DE)

(72) Inventors: Eric George Klauber, Huntsville, AL (US); Birgit Gockel, Ludwigshafen (DE); Sebastian Soergel, Limburgerhof (DE); Roland Goetz, Ludwigshafen (DE); Henricus Maria Martinus Bastiaans, Ludwigshafen (DE); Jochen Dietz, Ludwigshafen (DE); Joachim Gebhardt, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/347,414

(22) PCT Filed: Oct. 27, 2017

(86) PCT No.: PCT/EP2017/077657
§ 371 (c)(1),
(2) Date: May 3, 2019

(87) PCT Pub. No.: WO2018/083040
PCT Pub. Date: May 11, 2018

(65) Prior Publication Data
US 2019/0308954 A1   Oct. 10, 2019

(30) Foreign Application Priority Data

Nov. 4, 2016 (EP) ..................................... 16197197

(51) Int. Cl.
*C07D 403/12* (2006.01)
*A01N 43/58* (2006.01)

(52) U.S. Cl.
CPC .......... *C07D 403/12* (2013.01); *A01N 43/58* (2013.01)

(58) Field of Classification Search
CPC .............................. C07D 403/12; A01N 43/58
USPC ....................................................... 544/238
See application file for complete search history.

(56) References Cited

FOREIGN PATENT DOCUMENTS

| WO | 2012143317 A1 | 10/2012 |
|---|---|---|
| WO | 2015189080 A1 | 12/2015 |
| WO | 2016071243 A1 | 5/2016 |
| WO | 2016128239 A1 | 8/2016 |
| WO | 2016128240 A1 | 8/2016 |
| WO | 2016128261 A2 | 8/2016 |
| WO | 2016180614 A1 | 11/2016 |
| WO | 2016180642 A1 | 11/2016 |
| WO | 2016180833 A1 | 11/2016 |
| WO | 2016202807 A1 | 12/2016 |
| WO | 2017001252 A1 | 1/2017 |
| WO | 2017025377 A1 | 2/2017 |
| WO | 2017025454 A1 | 2/2017 |
| WO | 2017032580 A1 | 3/2017 |
| WO | 2017055386 A1 | 4/2017 |
| WO | 2017102905 A1 | 6/2017 |
| WO | 2017133942 A1 | 8/2017 |
| WO | 2017140614 A1 | 8/2017 |
| WO | 2017144336 A1 | 8/2017 |
| WO | 2017144337 A1 | 8/2017 |
| WO | 2017153218 A1 | 9/2017 |
| WO | 2017215928 A1 | 12/2017 |
| WO | 2017215929 A1 | 12/2017 |
| WO | 2018007175 A1 | 1/2018 |
| WO | 2018041665 A1 | 3/2018 |
| WO | 2018050518 A1 | 3/2018 |
| WO | 2018082962 A1 | 5/2018 |
| WO | 2018082964 A1 | 5/2018 |

OTHER PUBLICATIONS

Hawley,The Condensed Chemical Dictionary , 8th ed., .1971, p. 1-2 and 772. (Year: 1971).*
European Search Report for EP Patent Application No. 16197197.3, dated Jan. 19, 2017, 3 pages.
International Search Report for PCT Patent Application No. PCT/EP2017/077657, dated Dec. 7, 2017, 4 pages.
International Preliminary Report on Patentability dated May 7, 2019, prepared in International Application No. PCT/EP2017/077657.

* cited by examiner

*Primary Examiner* — Taylor V Oh
(74) *Attorney, Agent, or Firm* — Marshall, Gerstein & Borun LLP

(57) ABSTRACT

The present invention relates to a process for the purification of pyrazolpyridazines of formula I

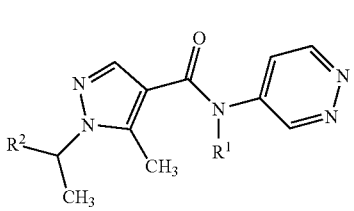

wherein the variables are as defined in the specification, by adding HCl to a solution of the pyrazolpyridazine in an inert solvent under non-aqueous conditions, effecting crystallization of the HCl-salt, isolating the resulting precipitate.

9 Claims, No Drawings

PROCESS FOR PURIFICATION OF PYRAZOLPYRIDAZINES

This application is a National Stage application of International Application No. PCT/EP2017/077657 filed Oct. 27, 2017. This application also claims priority under 35 U.S.C. § 119 to European Patent Application No. 16197197.3, filed Nov. 4, 2016.

The present invention relates to a process for the purification of pyrazolpyridazines of formula I

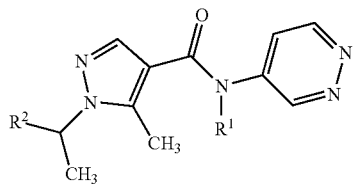

wherein
$R^1$ is H, $CH_3$, or $C_2H_5$; and
$R^2$ is $CH_3$, $CH(CH_3)_2$, $CHFCH_3$, $CF(CH_3)_2$, $CH(CH_3)CF_3$, $CHF_2$, or, 1-CN—$C_3H_4$;
by reacting HCl with a solution of the pyrazolpyridazine in an inert solvent, effecting crystallization of the HCl-salt, isolating the resulting precipitate being the HCl salt of formula I compound.

The pyrazolpyridazines of formula I can be obtained from the HCl salt by neutralization by adding a base to the salt, preferably to a solution of the salt in water, followed by extraction with an organic solvent.

The pyrazolpyridazines of formula I and their insecticidal activity are known from WO2012/143317. Although highly efficient manufacturing processes for such compounds are available, the raw product compound of formula I usually contains minor amounts of chemical compounds different from formula I that were created during synthesis as by-products, and hence there is ongoing need for purification of the active compound after synthesis.

It has been found that pure compound of formula I can be obtained from the process as defined in the outset by isolation of its HCl salt. The by-products and other impurities remain in solution whereas the HCl salt of formula I compound precipitates from the solution. The HCl salt of formula I compound is a 1:1 salt: one mole of formula I is associated with one mole HCl.

Another use for such process is to separate and collect pyrazolpyridazines of formula I from mother liquors obtained in the manufacturing process. By adding HCl to such mother liquor the HCl salt precipitates and can be separated in high purity. The synthesis of compounds of formula I is known from the art as referenced above. Mother liquors from the synthesis usually contain 1 to 5% by weight of formula I compounds and aliphatic and aromatic hydrocarbons as solvents, such as toluene, heptane, cyclohexane, xylenes, chlorobenezens, and alkyl acetates. Accordingly, this process is conducted by introducing HCl into such a solution of pyrazolpyridazines of formula I and precipitation of the respective formula I compound salt.

Pure means a content of at least 90%, preferably 95%, and more preferably 98% by weight of formula I pyrazolpyridazine salt. The pure salt consists of 90% by weight of formula I compound and 10% by weight of HCl. Impurities is counted any organic chemical material different from formula I salt. Purity is measured by HPLC of the free base and by elemental analysis of the salt.

The process for manufacture of the salt is carried out in a solvent wherein the formula I compound may be dissolved. Non-aqueous conditions are preferred to precipitate the salt from the solution, which means a water content in the solution of not more than 0.5%, preferably not more than 0.1% water per weight.

Suitable solvents are aliphatic hydrocarbons such as pentane, hexane, cyclohexane, and petrol ether, aromatic hydrocarbons such as toluene, o-, m-, and p-xylene, halogenated hydrocarbons such as methylene chloride, chloroform, and chlorobenzene, ethers such as diethylether, Diisopropylether, tert.-butylmethylether, dioxane, anisole, and tetrahydrofurane (THF), methyl-THF, cyclopentylmethylether, nitrils such as acetonitrile, and propionitrile, ketons such as acetone, methyl ethyl ketone, diethyl ketone, and tert.-butyl methyl ketone, moreover, dimethyl sulphoxide, dimethyl formamide, and dimethylacetamide, preferably aliphatic hydrocarbons, ethers such as dioxane, and aromatic hydrocarbons such as toluene, o-, m-, and p-xylene, particularly toluene. It is also possible to use mixtures of the solvents mentioned.

HCl is provided preferably in gaseous form. It is preferably introduced into the reaction mixture by bubbling it continuously through the solvent, wherein the production of the salt shall be performed, and wherein the formula I compound may already be dissolved. The HCl gas may be added via a dip-tube to make sure the gas is delivered to the solution. In this case, the dip-tube should preferably be fitted with a frit or filter to ensure that solid material does not impede the HCl addition. The HCl gas may be quenched in a scrubber containing a base once it left the reactor.

Alternatively, compound of formula I compound is dissolved in an organic solvent in a pressure reactor whereafter the reactor can be pressurized with 1.1 to 5 equiv of HCl, and then the reaction mixture is stirred until completion of the reaction. In this case the HCl gas is led onto the surface of the solution.

Alternatively, a reactor can be pressurized with 1.1 to 5 equiv of HCl, and then the formula I compound is added thereto. Preferably the formula I compound is added being dissolved in a solvent, and the reaction mixture is stirred until completion of the reaction. In this case the HCl gas is led onto the surface of the solution.

Alternatively, the HCl can be dissolved in an organic solvent, for example, dioxane, THF, diethyl ether or others, to which solution the formula I compound is added. Preferably the formula I compound is added being dissolved in a solvent, and the reaction mixture is stirred until completion of the reaction.

The amount of HCl itself is not particularly critical. In general, from 0.7 to 5 mol of HCl are used per mole of compound of formula I used, preferably from 0.8 to 2 mol of HCl per mole of compound I, more preferably from 0.9 to 1.3 mol of HCl per mole of compound I. The formation of the salt by means of HCl is effected generally at from −10 to 50° C., especially from 5 to 30° C., and at standard pressure or slightly elevated pressure, up to about 10, preferably 5, more preferably up to 3 bar.

HCl can be used in excess to the formula I compound to maximize the yield of the salt formation. For economic reasons, in order to minimize the amount of HCl needed, the process is preferably carried out in a closed pressure reactor. HCl gas is introduced preferably above the solution. Usually 1.05 to 5 mole equivalents HCl to formula I compound are sufficient for a complete crystallization of formula I salt;

more preferably 1.05 to 1.5 mole equivalents yield in a complete crystallization. The process is preferably carried out under the HCl pressure that develops during HCl addition. Preferably the solution is stirred during HCl addition to achieve a homogeneous HCl concentration in the solution.

For economical and practical reasons, the concentration of formula I compound is usually at least 10% and up to a saturated solution, the concentration in the saturated solution depends on the nature of the solvent and the temperature. For practical reasons a concentration from 15 to 25% by weight is preferred.

The process is carried out at temperatures of from −20° C. to 100° C., preferably from 0° C. to 40° C. It is preferably conducted in an inert solvent such as toluene, tetrahydrofurane (THF), or dioxane, in the presence of HCl in an amount of at least 1.0 mol equivalent.

The formula I compound can be used in form of its HCl salt, e.g. in agricultural formulations. If the formula I compound is being used as free base, the salt will be neutralized by adding about one mole of a base to the salt.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide, and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover, organic bases, for example tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Particular preference is given to $K_2CO_3$, NaOH, or triethylamine. The bases are generally employed in equimolar amounts, in excess or, if appropriate, as solvent.

If desired, it may be advantageous to remove the salt formed from HCl and formula I in the course of the neutralization before the further processing of formula I compounds, for example, by means of filtration methods. With regard to the filtration of the salt, a particularly advantageous procedure is that in the presence of a small water content (for example when the HCl gas is introduced). This generally gave rise to significantly shorter filtration times, which may be highly advantageous for the procedure on the industrial scale.

The process is particularly applicable to a compound selected from compounds I-1 to I-3 which are: 1-(1,2-dimethylpropyl)-N-ethyl-5-methyl-N-pyridazin-4-yl-pyrazole-4-carboxamide (I-1), 1-[1-(1-cyanocyclopropyl)ethyl]-N-ethyl-5-methyl-N-pyridazin-4-yl-pyrazole-4-carboxamide (I-2), and N-ethyl-1-(2-fluoro-1-methylpropyl)-5-methyl-N-pyridazin-4-yl-pyrazole-4-carboxamide (I-3).

The HCl salt can be directly used in any acidic agricultural formulations of the pyrazolpyridazine compound.

The invention also relates to agrochemical compositions comprising an auxiliary and at least one salt compound of the present invention or a mixture thereof.

An agrochemical composition comprises a pesticidally effective amount of a salt compound of the present invention or a mixture thereof. The term "pesticidally effective amount" is defined below.

The HCl salt compounds of formula I or the mixtures thereof can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

Preferred formulation types are: SL, SG, WP, OD, tablets, gel baits, CS (water in oil capsules), and Water in oil emulsions.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclo-hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl-naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Exam-ples of carboxylates are alkyl carboxylates, and carboxylated alcohol or alkylphenol eth-oxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types of the HCl salt (which is referred to "compound I" in the following examples) and their preparation are:

i) Water-Soluble Concentrates (SL, LS)
10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)
5-25 wt % of a compound I according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)
15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)
5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)
In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)
50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)
50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)
In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)
5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

x) Microcapsules (CS)
An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules.

xi) Dustable Powders (DP, DS)
1-10 wt % of a compound I according to the invention are ground finely and mixed intimately with up to 100 wt % solid carrier, e.g. finely divided kaolin.

xii) Granules (GR, FG)
0.5-30 wt % of a compound I according to the invention is ground finely and associated with up to 100 wt % solid carrier (e.g. silicate). Granulation is achieved by extrusion, spray-drying or the fluidized bed.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions com¬prising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage de-vice, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

EXAMPLES

The products shown below were characterized by NMR spectroscopy or by elemental analysis.
Dry toluene contains up to 500 ppm water.

Manufacture of 1-(1,2-dimethylpropyl)-N-ethyl-5-methyl-N-pyridazin-4-yl-pyrazole-4-carboxamide×1 HCl salt Example 1

A solution of 7.25 g of 1-(1,2-dimethylpropyl)-N-ethyl-5-methyl-N-pyridazin-4-yl-pyrazole-4-carboxamide (99% purity) in 28 g dry toluene was added to a nitrogen filled pressure reactor and stir at 25° C. HCl gas was slowly bubbled through for 1 h producing a thick slurry. The solution is allowed to stir for an additional hour at 20 to 25° C. The reactor is flushed with nitrogen and the slurry is filtered through nutsche. The salt is washed with toluene, then dried at 50° C. in a vacuum oven.

Yield: 8.00 g of the title compound salt

| Elemental analysis: (calculated for $C_{15}H_{22}N_5OCl$) | | |
|---|---|---|
| C | 56.9% | (56.5%) |
| H | 7.2% | (7.1%) |
| N | 20.6% | (21.3%) |
| O | 5.0% | (4.7%) |
| Cl | 10.2% | (10.4%) |

Example 2

A solution of 43.7 g of 1-(1,2-dimethylpropyl)-N-ethyl-5-methyl-N-pyridazin-4-yl-pyrazole-4-carboxamide (93.8% purity) in 215 g dry toluene was added to a nitrogen filled pressure reactor and stir at 25° C. The pressure reactor is charged with HCl gas (7.4 g (1.5 equiv)). The solution is allowed to stir for 2 hours at 20 to 25° C. producing a thick slurry. The reactor is depressurized, flushed with nitrogen and the slurry is filtered through nutsche. The salt is washed with toluene, then dried at 50° C. in a vacuum oven.

Yield: 28.0 g of the title compound salt

Example 3: Neutralization 2.00 g 1-(1,2-dimethylpropyl)-N-ethyl-5-methyl-N-pyridazin-1-ium-4-yl-pyrazole-4-carboxamide chloride were dissolved in 40 g water. The pH of the solution was adjusted from pH 1.6 to pH 5 with 2N NaOH. The solution was then extracted twice with 30 ml of toluene. Toluene was removed yielding 2.1 g of compound I-1 as an oil which contained 83.4% of compound I-1 and 16% toluene. The aqueous layer contained less than 0.1% of compound I-1.

The invention claimed is:
1. A process for purifying 1-(1,2-dimethylpropyl)-N-ethyl-5-methyl-N-pyridazin-4-yl-pyrazole-4-carboxamide ("compound I-1"), the process comprising:
  adding HCl to a solution of the compound I-1 in an inert solvent under non-aqueous conditions, thereby forming an HCl-salt of the compound I-1;
  effecting crystallization of the HCl-salt of the compound I-1, thereby forming a precipitate as a 1:1 HCl-salt of the compound I-1; and
  isolating the resulting precipitate.

2. The process of claim 1, wherein the solvent is selected from aliphatic solvents.

3. A process for purifying 1-(1,2-dimethylpropyl)-N-ethyl-5-methyl-N-pyridazin-4-yl-pyrazole-4-carboxamide ("compound I-1"), the process comprising:

adding HCl to a solution of the compound I-1 in an inert solvent under non-aqueous conditions, wherein the solvent is selected from the group consisting of toluene, o-, m-, and p-xylene, thereby forming an HCl-salt of the compound I-1;

effecting crystallization of the HCl-salt of the compound I-1, thereby forming a precipitate; and isolating the resulting precipitate.

4. The process of claim 1, wherein the concentration of the compound I-1 in the solvent is from 15 to 25% by weight.

5. The process of claim 1, further comprising neutralizing the HCl-salt of the compound I-1 with triethylamine, $K_2CO_3$, or NaOH.

6. A 1:1 HCl salt of 1-(1,2-dimethylpropyl)-N-ethyl-5-methyl-N-pyridazin-4-yl-pyrazole-4-carboxamide ("compound I-1").

7. An agricultural composition comprising:
at least one salt according to claim 6;
at least one inert liquid and/or solid acceptable carrier; and,
optionally at least one surfactant.

8. A process for purifying 1-(1,2-dimethylpropyl)-N-ethyl-5-methyl-N-pyridazin-4-yl-pyrazole-4-carboxamide ("compound I-1"), the process comprising:

adding HCl to a solution of the compound I-1 in an inert solvent under non-aqueous conditions, thereby forming an HCl-salt of the compound I-1, wherein:

the compound I-1 is initially present in the solution at a concentration in a range of 10 wt. % up to a saturation concentration of the compound I-1 in the inert solvent, the HCl is added to the solution in an amount of 1.05 to 5 mole equivalents HCl to compound I-1; and effecting crystallization of the HCl-salt of the compound I-1, thereby forming a precipitate; and isolating the resulting precipitate, wherein the isolated precipitate contains at least 98 wt. % of the HCl-salt of the compound I-1 as a 1:1 HCl salt.

9. The agricultural composition of claim 7, comprising the at least one surfactant.

* * * * *